(12) United States Patent
Auyeung et al.

(10) Patent No.: US 12,428,366 B2
(45) Date of Patent: Sep. 30, 2025

(54) PROCESS FOR PREPARING AN ALPHA-SUBSTITUTED ACRYLATE

(71) Applicant: DOW GLOBAL TECHNOLOGIES LLC, Midland, MI (US)

(72) Inventors: Evelyn Auyeung, Lake Jackson, TX (US); Arkady L. Krasovskiy, Lake Jackson, TX (US); Jaclyn Murphy, Ashland, MA (US); Bryan D. Stubbert, Midland, MI (US); Anna V. Davis, Auburn, MI (US); Clark H. Cummins, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 674 days.

(21) Appl. No.: 17/773,587

(22) PCT Filed: Dec. 17, 2020

(86) PCT No.: PCT/US2020/065764
§ 371 (c)(1),
(2) Date: Apr. 29, 2022

(87) PCT Pub. No.: WO2021/138073
PCT Pub. Date: Jul. 8, 2021

(65) Prior Publication Data
US 2022/0402856 A1 Dec. 22, 2022

Related U.S. Application Data

(60) Provisional application No. 62/954,956, filed on Dec. 30, 2019.

(51) Int. Cl.
C07C 67/343 (2006.01)

(52) U.S. Cl.
CPC .................................. *C07C 67/343* (2013.01)

(58) Field of Classification Search
CPC ........................... C07C 67/343; C07C 69/533
See application file for complete search history.

(56) References Cited

U.S. PATENT DOCUMENTS

| 3,687,922 A | 8/1972 | Gisser et al. |
| 4,370,343 A | 1/1983 | Mohrbacher et al. |
| 4,581,467 A * | 4/1986 | Malpass .................. C08F 4/602 |
| | | 556/170 |

FOREIGN PATENT DOCUMENTS

| DE | 102009028939 A1 | 3/2011 |
| JP | 1133529 | 12/1999 |
| WO | 2021138075 | 7/2021 |

OTHER PUBLICATIONS

Novak, et al. Nickel-catalysed asymmetric Sn2 substitution chemistry by Baylis-Hillman derived allylic electrophiles, Compter Rendus CHIMIE, Elsevier Masson SAS, (10), pp. 206-212 (Year: 2007).*

(Continued)

*Primary Examiner* — Yate' K Cutliff
(74) *Attorney, Agent, or Firm* — Karen L. Beckman

(57) ABSTRACT

The present disclosure relates to a process for preparing an alpha-substituted acrylate, the process comprising: a) combining starting materials comprising an alpha-(halomethyl) acrylate and an organoaluminum compound, thereby forming a product comprising the alpha-substituted acrylate.

12 Claims, 2 Drawing Sheets

(56) References Cited

OTHER PUBLICATIONS

Muller, D. S., et al., Tandem Hydroalumination/Cu-catalyzed asymmetric vinyl metalation as a new access to enantioenriched vinylcyclopropane derivatives, Organic letters, 19, pp. 3970-3973, and Supporting information, p. S1-S53 (Year: 2017).*
PCT/US2020/065764, International Search Report and Written Opinion with a mailing date of Apr. 19, 2021.
Langer, "Preparation and Reactions of New Dialkylzincs Obtained by a Boron-Zinc Transmetalation" 1993, vol. 34, No. 33, p. 5261-5264.
Milkiewicz, "Synthesis of a novel series of 10-oxa-3-aza-tricyclo[5.2.1.015]dec-8-en-4-ones through an intromolecular Diels-Alder reaction" 2003, vol. 44, No. 39, p. 7341-7343.
Muller, "Tandem Hydroalumination/Cu-Catalyzed Asymmetric Vinyl Metalation as a New Access to Enantioenriched Vinylcyclo-propane Derivatives" 2017, vol. 19, No. 15, p. 3970-3973.
Prasad, "The preparation of 1,3-dizincapropanes via a boron-zinc transmetallaion" 1998, p. 133-139.
Reichle, "Preparation of Alkylmagnesium Reagents from Alkenes through Hydroboration and Boron-Magnesium Exchange" 2012, vol. 51, No. 23, p. 5730-5734.
Office Action from corresponding Japanese application: 2022-539092 dated Sep. 11, 2024.

\* cited by examiner

PROCESS FOR PREPARING AN ALPHA-SUBSTITUTED ACRYLATE

CROSS-REFERENCE TO RELATED APPLICATIONS

The present application claims benefit of priority to U.S. Application No. 62/954,956, filed on Dec. 30, 2019, which is incorporated herein by reference in its entirety.

BACKGROUND

Alpha-substituted acrylates, such as alpha-(alkyl) acrylates or alpha-(polymeryl) acrylates, are important intermediates for preparing useful polymeric materials. Synthetic routes for the preparation of alpha-substituted acrylates and bisacrylates from organozinc reagents are known in the art. However, such routes employ transmetallation of organozinc compounds to organocopper compounds, and the direct reaction of organoaluminum compounds with halomethyl-acrylates is not known. The present disclosure addresses such a need by demonstrating a direct reaction of organoaluminum compounds with alpha-(halomethyl) acrylates to synthesize alpha-(alkyl) and alpha-(polymeryl) acrylates.

SUMMARY

The present disclosure is directed to a process for preparing an alpha-substituted acrylate, the process comprising:
a) combining starting materials comprising an alpha-(halomethyl) acrylate and an organoaluminum compound,
thereby forming a product comprising the alpha-substituted acrylate.

DETAILED DESCRIPTION

Definitions

Figure 1A:
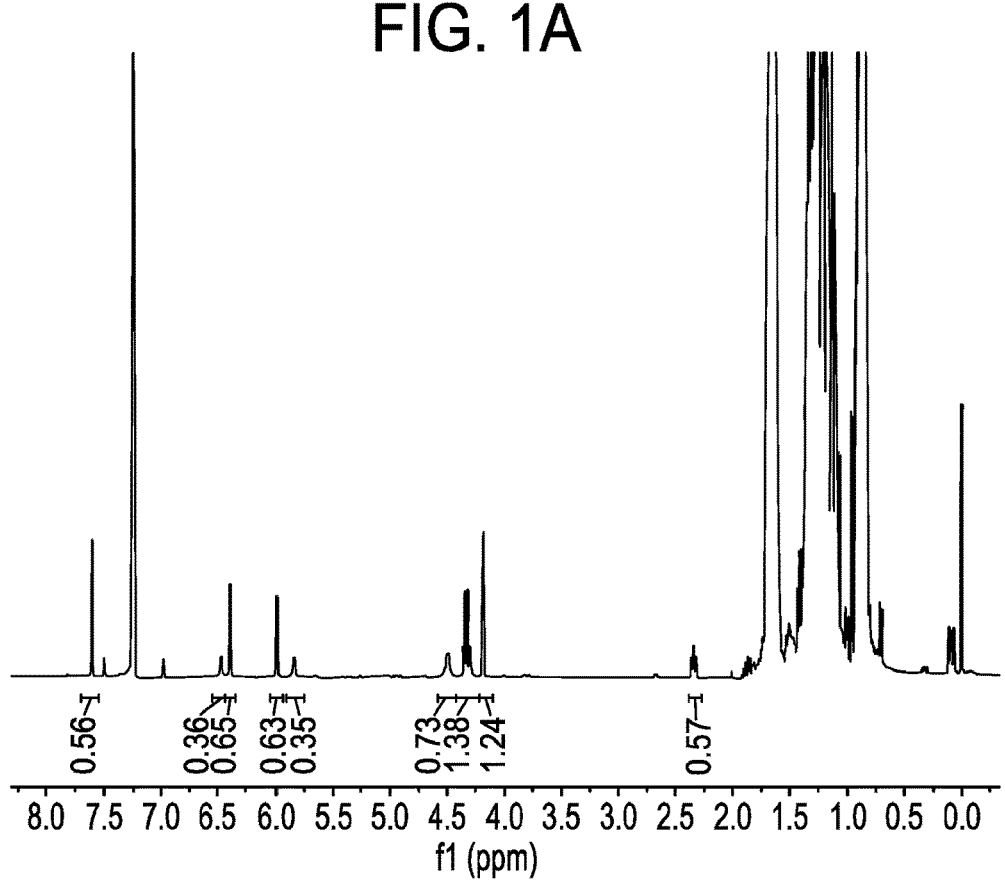
FIGS. 1A and 1B provide the NMR spectra for Example 1.

All references to the Periodic Table of the Elements herein shall refer to the Periodic Table of the Elements, published and copyrighted by CRC Press, Inc., 2003. Also, any references to a Group or Groups shall be to the Group or Groups reflected in this Periodic Table of the Elements using the IUPAC system for numbering groups.

Unless stated to the contrary, implicit from the context, or customary in the art, all parts and percents are based on weight.

For purposes of United States patent practice, the contents of any patent, patent application, or publication referenced herein are hereby incorporated by reference in their entirety (or the equivalent US version thereof is so incorporated by reference) especially with respect to the disclosure of synthetic techniques, definitions (to the extent not inconsistent with any definitions provided herein) and general knowledge in the art.

The numerical ranges disclosed herein include all values from, and including, the lower and upper value. For ranges containing explicit values (e.g., 1, or 2, or 3 to 5, or 6, or 7), any subrange between any two explicit values is included (e.g., 1 to 2; 2 to 6; 5 to 7; 3 to 7; 5 to 6; etc.). The numerical ranges disclosed herein further include the fractions between any two explicit values.

The terms "comprising," "including," "having" and their derivatives are not intended to exclude the presence of any additional component, step or procedure, whether or not the same is specifically disclosed. In contrast, the term "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination.

As used herein, the terms "hydrocarbyl," "hydrocarbyl group," and like terms refer to compounds composed entirely of hydrogen and carbon, including aliphatic, aromatic, acyclic, cyclic, polycyclic, branched, unbranched, saturated, and unsaturated compounds. The terms "hydrocarbyl," "hydrocarbyl group," "alkyl," "alkyl group," "aryl," "aryl group," and like terms are intended to include every possible isomer, including every structural isomer or stereoisomer.

The term "cyclic" refers to a series of atoms in a polymer or compound where such a series includes one or more rings. Accordingly, the term "cyclic hydrocarbyl group" refers to a hydrocarbyl group that contains one or more rings. A "cyclic hydrocarbyl group," as used herein, may contain acyclic (linear or branched) portions in addition to the one or more rings.

"Transmetalation" or "transmetallation" refers to an organometallic reaction involving the transfer of ligands from one metal to another.

The term "catalyst" is used interchangeably with "procatalyst," "precatalyst," "catalyst precursor," "transition metal catalyst," "transition metal catalyst precursor," "polymerization catalyst," "polymerization catalyst precursor," "transition metal complex." "transition metal compound," "metal complex," "metal compound," "complex," "metal-ligand complex," and like terms.

"Co-catalyst" refers to a compound that can activate certain procatalysts to form an active catalyst capable of polymerization of unsaturated monomers. The term "co-catalyst" is used interchangeably with "activator" and like terms.

"Active catalyst." "active catalyst composition," and like terms refer to a transition metal compound that is, with or without a co-catalyst, capable of polymerization of unsaturated monomers. An active catalyst may be a "procatalyst" that becomes active to polymerize unsaturated monomers without a co-catalyst. Alternatively, an active catalyst may a "procatalyst" that becomes active, in combination with a co-catalyst, to polymerize unsaturated monomers.

The term "polymer" refers to a material prepared by reacting (i.e., polymerizing) a set of monomers, wherein the set is a homogenous (i.e., only one type) set of monomers or a heterogeneous (i.e., more than one type) set of monomers. The term polymer as used herein includes the term "homopolymer," which refers to polymers prepared from a homogenous set of monomers, and the term "interpolymer" as defined below.

The term "interpolymer" refers to a polymer prepared by the polymerization of at least two different types of monomers. This term include both "copolymers." i.e., polymers prepared from two different types of monomers, and polymers prepared from more than two different types of monomers, e.g., terpolymers, tetrapolymers, etc. This term also embraces all forms of interpolymers, such as random, block, homogeneous, heterogeneous, etc.

A "polyolefin" is a polymer produced from the polymerization of an olefin as a monomer, where an olefin monomer is a linear, branched, or cyclic compound of carbon and hydrogen having at least one double bond. Accordingly, the term "polyolefin," as used herein, includes and covers the terms "ethylene-based polymer," "propylene-based polymer," "ethylene homopolymer," "propylene homopolymer," "ethylene/alpha-olefin interpolymer." "ethylene/alpha-olefin copolymer," "ethylene/alpha-olefin multiblock interpolymer," "block composite," "specified block composite." "crystalline block composite," "propylene/alpha-olefin interpolymer," and "propylene/alpha-olefin copolymer."

An "ethylene-based polymer" is a polymer that contains a majority amount of polymerized ethylene, based on the weight of the polymer, and, optionally, may further contain polymerized units of at least one comonomer. An "ethylene-based interpolymer" is an interpolymer that contains, in polymerized form, a majority amount of ethylene, based on the weight of the interpolymer, and further contains polymerized units of at least one comonomer. An "ethylene homopolymer" is a polymer that comprises repeating units derived from ethylene but does not exclude residual amounts of other components.

The term "ethylene/alpha-olefin interpolymer," as used herein, refers to a polymer that comprises, in polymerized form, a majority weight percent of ethylene (based on the weight of the interpolymer), and at least one comonomer that is an alpha-olefin. The ethylene/alpha-olefin interpolymer may be a random or block interpolymer. The terms "ethylene/alpha-olefin copolymer" and "ethylene/alpha-olefin multi-block interpolymer" are covered by the term "ethylene/alpha-olefin interpolymer."

The term "ethylene/alpha-olefin copolymer," as used herein, refers to a copolymer that comprises, in polymerized form, a majority weight percent of ethylene (based on the weight of the copolymer), and a comonomer that is an alpha-olefin, where ethylene and the alpha-olefin are the only two monomer types. The ethylene/alpha-olefin copolymer may be a random or block copolymer.

The term "ethylene/alpha-olefin multi-block interpolymer" or "olefin block copolymer," as used herein, refers to an interpolymer that includes ethylene and one or more copolymerizable alpha-olefin comonomers in polymerized form, characterized by multiple blocks or segments of two or more (preferably three or more) polymerized monomer units, the blocks or segments differing in chemical or physical properties. Specifically, this term refers to a polymer comprising two or more (preferably three or more) chemically distinct regions or segments (referred to as "blocks") joined in a linear manner, that is, a polymer comprising chemically differentiated units which are joined (covalently bonded) end-to-end with respect to polymerized functionality, rather than in pendent or grafted fashion. The blocks differ in the amount or type of comonomer incorporated therein, the density, the amount of crystallinity, the type of crystallinity (e.g., polyethylene versus polypropylene), the crystallite size attributable to a polymer of such composition, the type or degree of tacticity (isotactic or syndiotactic), region-regularity or region-irregularity, the amount of branching, including long chain branching or hyper-branching, the homogeneity, and/or any other chemical or physical property. The block copolymers are characterized by unique distributions of both polymer polydispersity (PDI or Mw/Mn) and block length distribution, e.g., based on the effect of the use of a shuttling agent(s) in combination with catalyst systems. Non-limiting examples of the olefin block copolymers of the present disclosure, as well as the processes for preparing the same, are disclosed in U.S. Pat. Nos. 7,858,706 B2, 8,198,374 B2, 8,318,864 B2, 8,609,779 B2, 8,710,143 B2, 8,785.551 B2, and 9,243,090 B2, which are all incorporated herein by reference in their entirety.

The term "block composite" ("BC") refers to a polymer comprising three polymer components: (i) an ethylene-based polymer (EP) having an ethylene content from 10 mol % to 90 mol % (a soft copolymer), based on the total moles of polymerized monomer units in the ethylene-based polymer (EP); (ii) an alpha-olefin-based polymer (AOP) having an alpha-olefin content of greater than 90 mol % (a hard copolymer), based on the total moles of polymerized monomer units in the alpha-olefin-based polymer (AOP); and (iii) a block copolymer (eblock copolymer) having an ethylene block (EB) and an alpha-olefin block (AOB); wherein the ethylene block of the block copolymer is the same composition as the EP of component (i) of the block composite and the alpha-olefin block of the block copolymer is the same composition as the AOP of component (ii) of the block composite. Additionally, in the block composite, the compositional split between the amount of EP and AOP will be essentially the same as that between the corresponding blocks in the block copolymer. Non-limiting examples of the block composites of the present disclosure, as well as processes for preparing the same, are disclosed in U.S. Pat. Nos. 8,686,087 and 8,716,400, which are incorporated herein by reference in their entirety.

The term "specified block composite" ("SBC") refers to a polymer comprising three polymer components: (i) an ethylene-based polymer (EP) having an ethylene content from 78 mol % to 90 mol % (a soft copolymer), based on the total moles of polymerized monomer units in the ethylene-based polymer (EP); (ii) an alpha-olefin-based polymer (AOP) having an alpha-olefin content of from 61 mol % to 90 mol % (a hard copolymer), based on the total moles of polymerized monomer units in the alpha-olefin-based polymer (AOP); and (iii) a block copolymer (diblock copolymer) having an ethylene block (EB) and an alpha-olefin block (AOB); wherein the ethylene block of the block copolymer is the same composition as the EP of component (i) of the specified block composite and the alpha-olefin block of the block copolymer is the same composition as the AOP of component (ii) of the specified block composite. Additionally, in the specified block composite, the compositional split between the amount of EP and AOP will be essentially the same as that between the corresponding blocks in the block copolymer. Non-limiting examples of the specified block composites of the present disclosure, as well as processes for preparing the same, are disclosed in WO 2017/044547, which is incorporated herein by reference in its entirety.

The term "crystalline block composite" ("CBC") refers to polymers comprising three components: (i) a crystalline ethylene based polymer (CEP) having an ethylene content of greater than 90 mol %, based on the total moles of polymerized monomer units in the crystalline ethylene based polymer (CEP); (ii) a crystalline alpha-olefin based polymer (CAOP) having an alpha-olefin content of greater than 90 mol %, based on the total moles of polymerized monomer units in the crystalline alpha-olefin based copolymer (CAOP); and (iii) a block copolymer comprising a crystalline ethylene block (CEB) and a crystalline alpha-olefin block (CAOB); wherein the CEB of the block copolymer is the same composition as the CEP of component (i) of the crystalline block composite and the CAOB of the block copolymer is the same composition as the CAOP of component (ii) of the crystalline block composite. Additionally, in the crystalline block composite, the compositional split between the amount of CEP and CAOP will be essentially the same as that between the corresponding blocks in the block copolymer. Non-limiting examples of the crystalline block composites of the present disclosure, as well as the processes for preparing the same, are disclosed in U.S. Pat. No. 8,822,598 B2 and WO 2016/01028961 A1, which are incorporated herein by reference in its entirety.

A "propylene-based polymer" is a polymer that contains a majority amount of polymerized propylene, based on the weight of the polymer, and, optionally, may further contain polymerized units of at least one comonomer. A "propylene-based interpolymer" is an interpolymer that contains, in polymerized form, a majority amount of propylene, based on the weight of the interpolymer, and further contains polymerized units of at least one comonomer. A "propylene homopolymer" is a polymer that comprises repeating units derived from propylene but does not exclude residual amounts of other components.

The term "propylene/alpha-olefin interpolymer," as used herein, refers to a polymer that comprises, in polymerized form, a majority weight percent of propylene (based on the weight of the interpolymer), and at least one comonomer that is an alpha-olefin (where ethylene is considered an alpha-olefin). The propylene/alpha-olefin interpolymer may be a random or block interpolymer. The term "propylene/alpha-olefin interpolymer" includes the term "propylene/alpha-olefin copolymer."

The term "propylene/alpha-olefin copolymer," as used herein, refers to a copolymer that comprises, in polymerized form, a majority weight percent of propylene (based on the weight of the copolymer), and a comonomer that is an alpha-olefin, wherein propylene and the alpha-olefin are the only two monomer types. The propylene/alpha-olefin copolymer may be a random or block copolymer.

The terms "polymeryl," "polymeryl group" and like terms refer to a polymer missing one hydrogen.

The terms "polyolefinyl," "polyolefinyl group" and like terms refer to a polyolefin missing one hydrogen.

Alpha-(halomethyl) acrylate

The starting materials of step a) of the process of the present disclosure comprise an alpha-(halomethyl) acrylate. In certain embodiments, the alpha-(halomethyl) acrylate has the formula (II):

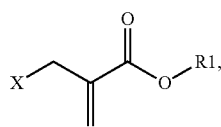

(II)

wherein:
X is a halogen; and
R1 is a C1-C30 hydrocarbyl group.

In certain embodiments, X is a halogen and is selected from the group consisting of fluoride, chloride, bromide, and iodide.

In certain embodiments, R1 is a C1-C30 hydrocarbyl group that may be linear branched, or cyclic. In further embodiments, R1 is a C1-C30 alkyl group that may be linear, branched, or cyclic. For example, R1 may be a linear, branched, or cyclic alkyl group comprising from 1 to 30 carbon atoms, or from 1 to 20 carbon atoms, or from 1 to 10 carbon atoms, or from 1 to 8 carbon atoms, or from 1 to 3 carbon atoms.

Organoaluminum Compound

The starting materials of step a) of the process of the present disclosure comprise an organoaluminum compound of the formula $R_3Al$, wherein each R independently is a C1-C26 hydrocarbyl group or a polyolefinyl group.

In certain embodiments, each R of the organoaluminum compound of the formula $R_3Al$ independently is a C1-C26 hydrocarbyl group. In certain embodiments, each R of the organoaluminum compound of the formula $R_3Al$ independently is a C1-C26 hydrocarbyl group that may be linear, branched, or cyclic. In further embodiments, each R of the organoaluminum compound of the formula $R_3Al$ independently is a C1-C26 alkyl group that may be linear, branched, or cyclic. For example, each R of the organoaluminum compound of the formula R3Al may independently be a linear, branched, or cyclic alkyl group comprising from 1 to 26 carbon atoms, or from 1 to 10 carbon atoms, or from 1 to 8 carbon atoms.

In some embodiments, each R of the organoaluminum compound of the formula $R_3Al$ independently is a polyolefinyl group. In further embodiments, each R of the organoaluminum compound of the formula $R_3Al$ independently is a polyolefinyl group, which can be defined by the properties of R—H, wherein R—H has a number average molecular weight of greater than 365 g/mol. In further embodiments, each R of the organoaluminum compound of the formula $R_3Al$ independently is a polyolefinyl group, which can be defined by the properties of R—H, wherein R—H has a number average molecular weight from greater than 365 g/mol to 10,000,000 g/mol, or from greater than 365 g/mol to 5,000,000 g/mol, or from greater than 365 g/mol to 1,000,000 g/mol, or from greater than 365 g/mol to 750,000 g/mol, or from greater than 365 g/mol to 500,000 g/mol, or from greater than 365 g/mol to 250,000 g/mol.

In further embodiments, each R of the organoaluminum compound of the formula $R_3Al$ independently is a polyolefinyl group, which can be defined by the properties of R—H, wherein R—H has a density from 0.850 to 0.965 g/cc, or from 0.860 to 0.950 g/cc, or from 0.865 to 0.925 g/cc.

In further embodiments, each R of the organoaluminum compound of the formula $R_3Al$ independently is a polyolefinyl group, which can be defined by the properties of R—H, wherein R—H has a melt index (I2) from 0.01 to 2,000 g/10 minutes, or from 0.01 to 1,500 g/10 minutes, or from 0.1 to 1,000 g/10 minutes, or from 0.1 to 500 g/10 minutes, or from 0.1 to 100 g/10 minutes.

In further embodiments, each R of the organoaluminum compound of the formula $R_3Al$ independently is a polyolefinyl group, which can be defined by the properties of R—H, wherein R—H has a number average molecular weight distribution (Mw/Mn or PDI) from 1 to 10, or from 1 to 7, or from 1 to 5, or from 2 to 4.

In certain embodiments, each R of the organoaluminum compound of the formula $R_3Al$ independently is an ethylene homopolymeryl group comprising units derived from ethylene.

In certain embodiments, each R of the organoaluminum compound of the formula $R_3Al$ independently is an ethylene/alpha-olefin interpolymeryl group comprising units derived from ethylene and at least one C3-C30 alpha-olefin. The C3-C30 alpha-olefin may be, for example, 1-butene, 4-methyl-1-pentene, 1-hexene, 1-octene, 1-decene, 1-dodecene, 1-tetradecene, 1-hexadecene, or 1-octadecene.

In certain embodiments, each R of the organoaluminum compound of the formula $R_3Al$ independently is an ethylene/alpha-olefin copolymeryl group comprising units derived from ethylene and a C3-C30 alpha-olefin. The C3-C30 alpha-olefin may be, for example, propylene, 1-butene, 4-methyl-1-pentene, 1-hexene, 1-octene, 1-decene, 1-dodecene, 1-tetradecene, 1-hexadecene, or 1-octadecene.

In certain embodiments, each R of the organoaluminum compound of the formula $R_3Al$ independently is an ethylene/alpha-olefin multi-block interpolymeryl group or olefin block copolymeryl group as defined herein.

In further embodiments, each R of the organoaluminum compound of the formula R3Al independently is a polymeryl group of a block composite, a specified block composite, or a crystalline block composite, as defined herein.

In certain embodiments, each R of the organoaluminum compound of the formula $R_3Al$ independently is a propylene homopolymeryl group comprising units derived from propylene.

In certain embodiments, each R of the organoaluminum compound of the formula $R_3Al$ independently is a propylene/alpha-olefin interpolymeryl group comprising units derived from propylene and at least one comonomer that is ethylene or a C3-C30 alpha-olefin. The C3-C30 alpha-olefin may be, for example, propylene, 1-butene, 4-methyl-1-pentene, 1-hexene, 1-octene, 1-decene, 1-dodecene, 1-tetradecene, 1-hexadecene, or 1-octadecene.

In certain embodiments, each R of the organoaluminum compound of the formula $R_3Al$ independently is a propylene/alpha-olefin copolymeryl group comprising units derived from propylene and a comonomer that is ethylene or a C3-C30 alpha-olefin. The C3-C30 alpha-olefin may be, for example, propylene, 1-butene, 4-methyl-1-pentene, 1-hexene, 1-octene, 1-decene, 1-dodecene, 1-tetradecene, 1-hexadecene, or 1-octadecene.

Regarding the embodiments wherein each R of the organoaluminum compound of the formula $R_3Al$ independently is a polyolefinyl group, the organoaluminum compound of the formula $R_3Al$ may be prepared by a process (a1), wherein the process (a1) comprises combining starting materials comprising:

i) an olefin monomer component;
ii) a catalyst; and
iii) a chain shuttling agent of the formula $J_3Al$, wherein each J independently is a C1-C20 hydrocarbyl group, thereby forming a solution or slurry comprising the organoaluminum compound of the formula $R_3Al$.

Starting material i), the olefin monomer component, comprises one or more olefin monomers. Suitable olefin monomers include straight chain or branched alpha-olefins of 2 to 30 carbon atoms, alternatively 2 to 20 carbon atoms, such as ethylene, propylene, 1-butene, 3-methyl-1-butene, 1-pentene, 1-hexene, 4-methyl-1-pentene, 3-methyl-1-pentene, 1-octene, 1-decene, 1-dodecene, 1-tetradecene, 1-hexadecene, 1-octadecene, and 1-eicosene; cycloolefins of 3 to 30, alternatively 3 to 20 carbon atoms such as cyclopentene, cycloheptene, norbornene, 5-methyl-2-norbornene, tetracyclododecene, and 2-methyl-1,4,5,8-dimethano-1,2,3,4,4a,5,8,8a-octahydronaphthalene. Suitable olefin monomers are disclosed for example, at col. 16, lines 5-36 of U.S. Pat. No. 7,858,706 and at col. 12, lines 7 to 41 of U.S. Pat. No. 8,053,529, which are hereby incorporated by reference. In certain embodiments, starting material i) may comprise ethylene and optionally one or more olefin monomers other than ethylene, such as propylene or 1-octene.

Regarding starting material ii), suitable catalysts include any compound or combination of compounds that is adapted for preparing polymers of the desired composition or type. One or more catalysts may be used. For example, first and second olefin polymerization catalysts may be used for preparing polymers differing in chemical or physical properties. Both heterogeneous and homogeneous catalysts may be employed. Examples of heterogeneous catalysts include Ziegler-Natta compositions, especially Group 4 metal halides supported on Group 2 metal halides or mixed halides and alkoxides and chromium or vanadium based catalysts. Alternatively, for ease of use and for production of narrow molecular weight polymer segments in solution, the catalysts may be homogeneous catalysts comprising an organometallic compound or metal complex, such as compounds or complexes based on metals selected from Groups 3 to 15 or the Lanthanide series of the Periodic Table of the Elements. Starting material ii) may further comprise a cocatalyst in addition to the catalyst. The cocatalyst may be a cation forming co-catalyst, a strong Lewis Acid, or combination thereof. Suitable catalysts and cocatalysts are disclosed, for example, at col. 19, line 45 to col. 51, line 29 of U.S. Pat. No. 7,858,706, and col. 16, line 37 to col. 48, line 17 of U.S. Pat. No. 8,053,529, which are hereby incorporated by reference. Suitable procatalysts that may also be added include but are not limited to those disclosed in PCT Publications WO 2005/090426, WO 2005/090427, WO 2007/035485, WO 2009/012215, WO 2014/105411, WO 2017/173080, U.S. Patent Publication Nos. 2006/0199930, 2007/0167578, 2008/0311812, and U.S. Pat. Nos. 7,355,089 B2, 8,058,373 B2, and 8,785,554 B2.

Regarding starting material iii), the chain shuttling agent has the formula $J_3Al$, where each J is independently a hydrocarbyl group of 1 to 20 carbon atoms. The hydrocarbyl group for J has 1 to 20 carbon atoms, alternatively 2 to 12 carbon atoms. The hydrocarbyl group for J may be an alkyl group, which may be linear or branched. J may be an alkyl group exemplified by ethyl, propyl, octyl, and combinations thereof. Suitable chain shuttling agents include trialkyl aluminum compounds, such as triethyl aluminum. Suitable chain shuttling agents are disclosed at col. 16, line 37 to col. 19, line 44 of U.S. Pat. No. 7,858,706 and col. 12, line 49 to col. 14, line 40 of U.S. Pat. No. 8,053,529, which are hereby incorporated by reference.

The starting materials for preparing the organoaluminum compound of the formula $R_3Al$ may optionally further comprise one or more additional starting materials selected from: iv) a solvent, vi) a scavenger, vii) an adjuvant, and viii) a polymerization aid. Toluene and Isopar™ E are examples of solvents for starting material iv). Isopar™ E is an isoparaffin fluid, typically containing less than 1 ppm benzene and less than 1 ppm sulfur, which is commercially available from ExxonMobil Chemical Company.

The process conditions and equipment for preparing the organoaluminum compound of the formula $R_3Al$ are known in the art and are disclosed, for example in U.S. Pat. Nos. 7,858,706 and 8,053,529, which are hereby incorporated by reference. For example, the process (a1) may be characterized as polymerization that is desirably carried out as a continuous polymerization, preferably a continuous, solution polymerization, in which catalyst components, shuttling agent(s), monomers, and optionally solvent, adjuvants, scavengers, and polymerization aids are continuously supplied to the reaction zone and polymer product continuously removed there from. Within the scope of the terms "continuous" and "continuously" as used in this context are those processes in which there are intermittent additions of reactants and removal of products at small regular or irregular intervals, so that, over time, the overall process is substantially continuous.

The polymerization can be advantageously employed as a high pressure, solution, slurry, or gas phase polymerization process. For a solution polymerization process it is desirable to employ homogeneous dispersions of the catalyst components in a liquid diluent in which the polymer is soluble under the polymerization conditions employed. One such process utilizing an extremely fine silica or similar dispersing agent to produce such a homogeneous catalyst dispersion where either the metal complex or the cocatalyst is only poorly soluble is disclosed in U.S. Pat. No. 5,783,512. A solution process to prepare the novel polymers of the present invention, especially a continuous solution process is preferably carried out at a temperature between 80° C. and 250° C., more preferably between 100° C. and 210° C., and most preferably between 110° C. and 210° C. A high pressure process is usually carried out at temperatures from 100° C. to 400° C. and at pressures above 500 bar (50 MPa). A slurry process typically uses an inert hydrocarbon diluent and temperatures of from 0° C. up to a temperature just below the temperature at which the resulting polymer becomes substantially soluble in the inert polymerization medium. Preferred temperatures in a slurry polymerization are from 30° C., preferably from 60° C. up to 115° C., preferably up to 100° C. Pressures typically range from atmospheric (100 kPa) to 500 psi (3.4 Mpa).

Preparing an Alpha-Substituted Acrylate

The present process is directed to preparing an alpha-substituted acrylate. In certain embodiments, the alpha-substituted acrylate has the formula (I):

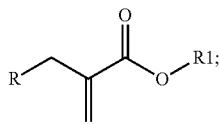

(I)

wherein R is a C1-C26 hydrocarbyl group or a polyolefinyl group; and

R1 is a C1-C30 hydrocarbyl group.

Each of the R and R1 groups of the alpha-substituted acrylate of the formula (I) is the same as and includes all embodiments of the R group of the organoaluminum compound of the formula $R_3Al$ and the R1 group of the alpha-(halomethyl) acrylate of the formula (II), respectively. Indeed, the process of the present disclosure relates to a nucleophilic substitution reaction whereby X, the halogen, is a leaving group that is replaced by an R of the organoaluminum compound of the formula $R_3Al$.

In certain embodiments, step a) of the process of the present disclosure may be performed neat. In further embodiments, the starting materials in step a) of the process of the present disclosure further comprise a hydrocarbon solvent. In further embodiments, the starting materials in step a) of the process of the present disclosure further comprise a hydrocarbon solvent that is a non-aromatic hydrocarbon solvent.

In some embodiments, step a) of the process of the present disclosure is performed at a temperature that is above the melting temperature of the R group as defined herein. For example and without limitation, step a) of the process of the present disclosure may be performed at a temperature from 15° C. to 100° C.

In some embodiments, the ratio of the alpha-(halomethyl) acrylate to the organoaluminum compound of the formula $R_3Al$ in step a) is 15:1, or 12:1, or 9:1, or 6:1, or 3:1, or 2:1, or 1:1.

In preferred embodiments, the process of the present disclosure excludes any transmetallation step or reaction.

In certain embodiments, step a) of the process of the present disclosure is uncatalyzed. In further embodiments, step a) of the process of the present disclosure may be catalyzed by one or more organocatalysts. An organocatalysts is a catalyst that excludes any metal elements. Accordingly, in certain embodiments, the starting materials in step a) of the present process further comprises an organocatalyst. For example, the starting materials in step a) of the process of the present disclosure further comprises a nitrogen containing heterocycle as disclosed in WO 2019/182992. The nitrogen containing heterocycle can be, for example and without limitation, N-methyl imidazole.

Specific embodiments of the present disclosure include but are not limited to the following:

1. A process for preparing an alpha-substituted acrylate, the process comprising:
   a) combining starting materials comprising an alpha-(halomethyl) acrylate and an organoaluminum compound,
   thereby forming a product comprising the alpha-substituted acrylate.

2. A process for preparing an alpha-substituted acrylate, the process comprising:
   a) combining starting materials comprising an alpha-(halomethyl) acrylate and an organoaluminum compound of the formula $R_3Al$,
   thereby forming a product comprising the alpha-substituted acrylate, wherein:
   the alpha-substituted acrylate has the formula (I):

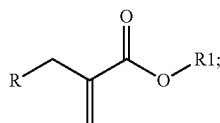

(I)

the alpha-(halomethyl) acrylate has the formula (II):

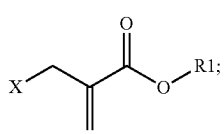

(II)

each R independently is a C1-C26 hydrocarbyl group or a polyolefinyl group;

each R1 independently is a C1-C30 hydrocarbyl group; and

X is a halogen.

i. The process of embodiment 1 or 2, wherein the starting materials of step a) further comprise a solvent.

4. The process of embodiment 3, wherein the solvent is a non-aromatic hydrocarbon solvent.

5. The process of any of the previous embodiments, wherein the process excludes any transmetallation step or reaction.

6. The process of any of the previous embodiments, wherein the starting materials of step a) further comprise an organocatalyst.

7. The process of embodiment 6, wherein the organocatalyst is a nitrogen containing heterocycle.

8. The process of embodiment 7, wherein the nitrogen containing heterocycle is N-methyl imidazole.

9. The process of any of the previous embodiments, wherein each R1 independently is a C1-C30, or C1-C10, or C1-C8, or C1-C3 alkyl group that is linear, branched, or cyclic.

10. The process of any of the previous embodiments, wherein each R independently is a C1-C30 hydrocarbyl group.

11. The process of embodiment 10, wherein each R independently is a C1-C30, or C1-C10, or C1-C8 alkyl group that is linear, branched, or cyclic.

12. The process of any of embodiments 1-9, wherein each R independently is a polyolefinyl group.

13. The process of embodiment 12, wherein the polyolefinyl group is an ethylene-based polymeryl group.

14. The process of embodiment 13, wherein the polyolefinyl group is an ethylene homopolymeryl group comprising units derived from ethylene.

15. The process of embodiment 13, wherein the polyolefinyl group is an ethylene/alpha-olefin interpolymeryl group comprising units derived from ethylene and a C3-C30 alpha-olefin.

16. The process of embodiment 13, wherein the polyolefinyl group is an ethylene/alpha-olefin copolymeryl group comprising units derived from ethylene and a C3-C30 alpha-olefin.

17. The process of embodiments 15 or 16, wherein the C3-C30 alpha-olefin is selected from the group consisting of propylene, 1-butene, 1-hexene, and 1-octene.

18. The process of embodiment 13, wherein the polyolefinyl group is an ethylene/alpha-olefin multiblock interpolymeryl group.

19. The process of embodiment 13, wherein the polyolefinyl group is selected from the group consisting of a polymeryl group of a block composite, a polymeryl group of a specified block composite, and a polymeryl group of a crystalline block composite.

20. The process of embodiment 12, wherein the polyolefinyl group is a propylene-based polymeryl group.

21. The process of embodiment 20, wherein the polyolefinyl group is a propylene homopolymeryl group comprising units derived from propylene.

22. The process of embodiment 20, wherein the polyolefinyl group is a propylene/alpha-olefin interpolymeryl group comprising units derived from propylene and either ethylene or a C4-C30 alpha-olefin.

23. The process of embodiment 20, wherein the polyolefinyl group is a propylene/alpha-olefin copolymeryl group comprising units derived from propylene and either ethylene or a C4-C30 alpha-olefin.

24. The process of embodiment 22 or 23, wherein the C4-C30 alpha-olefin is selected from the group consisting of 1-butene, 1-hexene, and 1-octene.

25. The process of any of embodiments 12-24, wherein the polyolefinyl group can be defined by properties of R—H, and wherein R—H has a number average molecular weight of greater than 365 g/mol.

26. The process of any of embodiments 12-25, wherein the polyolefinyl group can be defined by properties of R—H, and wherein R—H has a number average molecular weight of from greater than 365 g/mol to 10,000,000 g/mol, or from greater than 365 g/mol to 5,000,000 g/mol, or from greater than 365 g/mol to 1,000.000 g/mol, or from greater than 365 g/mol to 750,000 g/mol, or from greater than 365 g/mol to 500,000 g/mol, or from greater than 365 g/mol to 250.000 g/mol.

27. The process of any of embodiments 12-26, wherein the polyolefinyl group can be defined by properties of R—H, and wherein R—H has a density from 0.850 to 0.965 g/cc, or from 0.860 to 0.950 g/cc, or from 0.865 to 0.925 g/cc.

28. The process of any of embodiments 12-27, wherein the polyolefinyl group can be defined by properties of R—H. and wherein R—H has a melt index (I2) from 0.01 to 2.000 g/10 minutes, or from 0.01 to 1,500 g/10 minutes, or from 0.1 to 1,000 g/10 minutes, or from 0.1 to 500 g/10 minutes, or from 0.1 to 100 g/10 minutes.

29. The process of any of embodiments 12-28, wherein the polyolefinyl group can be defined by properties of R—H, and wherein R—H has a number average molecular weight distribution (Mw/Mn) from 1 to 10, or from 1 to 7, or from 1 to 5, or from 2 to 4.

30. The process of any of the previous embodiments, wherein step a) is performed at a temperature from 15° C. to 100° C.

31. The process of any of the previous embodiments, wherein the ratio of the alpha-(halomethyl) acrylate to the organoaluminum compound in step a) is 15:1, or 12:1, or 9:1, or 6:1, or 3:1, or 2:1, or 1:1.

32. The process of embodiment 1, wherein the organoaluminum compound is prepared by a process comprising combining starting materials comprising:
i) an olefin monomer component; ii) a catalyst; and iii) a chain shuttling agent,
thereby forming a solution or slurry comprising the organoaluminum compound.

33. The process of any of embodiments 2-31, wherein the organoaluminum compound of the formula $R_3Al$ is prepared by a process comprising combining starting materials comprising:
i) an olefin monomer component; ii) a catalyst; and iii) a chain shuttling agent of the formula $J_3Al$, wherein each J independently is a C1-C20 hydrocarbyl group.
thereby forming a solution or slurry comprising the organoaluminum compound of the formula $R_3Al$.

Test Methods

Density:

Density is measured in accordance with ASTM D-792, Method B.

Melt Index:

Melt index ($I_2$) is measured in accordance with ASTM D-1238, which is incorporated herein by reference in its entirety, Condition 190° C./2.16 kg, and was reported in grams eluted per 10 minutes.

GPC:

Sample polymers were tested for their properties via GPC according to the following.

A high temperature Gel Permeation Chromatography system (GPC IR) consisting of an Infra-red concentration detector (IR-5) from PolymerChar Inc (Valencia, Spain) was used for Molecular Weight (MW) and Molecular Weight Distribution (MWD) determination. The carrier solvent was 1,2,4-trichlorobenzene (TCB). The auto-sampler compartment was operated at 160° C., and the column compartment was operated at 150° C. The columns used were four Polymer Laboratories Mixed A LS, 20 micron columns. The chromatographic solvent (TCB) and the sample preparation solvent were from the same solvent source with 250 ppm of butylated hydroxytoluene (BHT) and nitrogen sparged. The samples were prepared at a concentration of 2 mg/mL in TCB. Polymer samples were gently shaken at 160° C. for 2 hours. The injection volume was 200 μl, and the flow rate was 1.0 ml/minute.

Calibration of the GPC column set was performed with 21 narrow molecular weight distribution polystyrene standards. The molecular weights of the standards ranged from 580 to 8,400,000 g/mol, and were arranged in 6 "cocktail" mixtures, with at least a decade of separation between individual molecular weights.

The GPC column set was calibrated before running the examples by running twenty-one narrow molecular weight distribution polystyrene standards. The molecular weight (Mw) of the standards ranges from 580 to 8,400,000 grams per mole (g/mol), and the standards were contained in 6 "cocktail" mixtures. Each standard mixture had at least a decade of separation between individual molecular weights. The standard mixtures were purchased from Polymer Laboratories (Shropshire, UK). The polystyrene standards were prepared at 0.025 g in 50 mL of solvent for molecular weights equal to or greater than 1,000,000 g/mol and 0.05 g in 50 mL of solvent for molecular weights less than 1,000,000 g/mol. The polystyrene standards were dissolved at 80° C. with gentle agitation for 30 minutes. The narrow standards mixtures were run first and in order of decreasing highest molecular weight (Mw) component to minimize degradation. The polystyrene standard peak molecular weights were converted to polyethylene Mw using the Mark-Houwink constants. Upon obtaining the constants, the two values were used to construct two linear reference conventional calibrations for polyethylene molecular weight and polyethylene intrinsic viscosity as a function of elution column.

The polystyrene standard peak molecular weights were converted to polyethylene molecular weights using the following equation (as described in Williams and Ward, J. Polym. Sci., Polym. Let., 6, 621 (1968)):

$$M_{polyethylene} = A(M_{polystyrene})^B \quad (1)$$

Here B has a value of 1.0, and the experimentally determined value of A is around 0.41.

A third order polynomial was used to fit the respective polyethylene-equivalent calibration points obtained from equation (1) to their observed elution volumes of polystyrene standards.

Number, weight, and z-average molecular weights were calculated according to the following equations:

$$\overline{Mn} = \frac{\Sigma^i W f_i}{\Sigma^i (W f_i / M_i)} \quad (2)$$

$$\overline{Mw} = \frac{\Sigma^i (W f_i * M_i)}{\Sigma^i W f_i} \quad (3)$$

$$\overline{Mz} = \frac{\Sigma^i (W f_i * M_i^2)}{\Sigma^i (W f_i * M_i)} \quad (4)$$

Where, $Wf_i$ is the weight fraction of the i-th component and $M_i$ is the molecular weight of the i-th component.

The MWD was expressed as the ratio of the weight average molecular weight (Mw) to the number average molecular weight (Mn).

The accurate A value was determined by adjusting A value in equation (1) until Mw calculated using equation (3) and the corresponding retention volume polynomial, agreed with the known Mw value of 120,000 g/mol of a standard linear polyethylene homopolymer reference.

The GPC system consists of a Waters (Milford, Mass.) 150° C. high temperature chromatograph (other suitable high temperatures GPC instruments include Polymer Laboratories (Shropshire, UK) Model 210 and Model 220) equipped with an on-board differential refractometer (RI). Additional detectors could include an IR4 infra-red detector from Polymer ChAR (Valencia, Spain), Precision Detectors (Amherst, Mass.) 2-angle laser light scattering detector Model 2040, and a Viscotek (Houston, Tex.) 150R 4-capillary solution viscometer. A GPC with the last two independent detectors and at least one of the first detectors is sometimes referred to as "3D-GPC", while the term "GPC" alone generally refers to conventional GPC. Depending on the sample, either the 15-degree angle or the 90-degree angle of the light scattering detector was used for calculation purposes.

Data collection was performed using Viscotek TriSEC software, Version 3, and a 4-channel Viscotek Data Manager DM400. The system was equipped with an on-line solvent degassing device from Polymer Laboratories (Shropshire, UK). Suitable high temperature GPC columns could be used, such as four 30 cm long Shodex HT803 13 micron columns or four 30 cm Polymer Labs columns of 20-micron mixed-pore-si ze packing (MixA LS, Polymer Labs). The sample carousel compartment was operated at 140° C. and the column compartment was operated at 150° C. The samples were prepared at a concentration of 0.1 grams of polymer in 50 milliliters of solvent. The chromatographic solvent and the sample preparation solvent contain 200 ppm of butylated hydroxytoluene (BHT). Both solvents were sparged with nitrogen. The polyethylene samples were gently stirred at 160° C. for four hours (4 h). The injection volume was 200 microliters (μL). The flow rate through the GPC was set at 1 mL/minute.

NMR ($^{13}$C and $^1$H):

NMR analysis was performed at room temperature using a standard NMR solvent, such as chloroform or benzene, and data was acquired on a Varian 500 MHz spectrometer.

GCMS:

Tandem gas chromatography/low resolution mass spectroscopy using electron impact ionization (EI) is performed at 70 eV on an Agilent Technologies 6890N series gas chromatograph equipped with an Agilent Technologies 5975 inert XL mass selective detector and an Agilent Technologies Capillary column (HP1MS, 15 m×0.25 mm, 0.25 micron) with respect to the following:

Programed Method:
  Oven Equilibration Time at 50° C. for 0.5 min
  then 25° C./min to 200° C., and hold for 5 min
  Run Time 11 min

EXAMPLES

The following examples are intended to illustrate some embodiments of the invention and should not be interpreted as limiting the scope of the invention set forth in the claims.

Unless stated otherwise, all materials and reagents are commercially available, such as from Sigma Aldrich.

Example 1

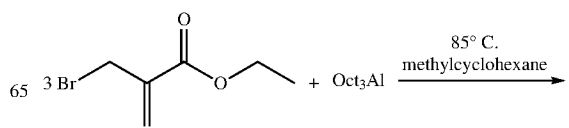

-continued

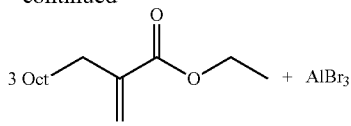

The reaction of Example 1 was performed under an inert nitrogen atmosphere glovebox and in accordance with the above reaction scheme which is exemplary and non-limiting. To the solution of ethyl bromomethyl acrylate (193 mg) in dry methylcyclohexane (5 mL) in a 20 mL vial solution of Oct3Al (122.5 mg, 0.33 equiv) was slowly added at RT. Reaction mixture turned slightly yellow, after overnight at room temperature color disappeared. 1,3,5-tribromobenzene was added (76 mg, 0.244 mmol) was added as internal standard.

After 12 hours at room temperature the NMR conversion was calculated to be ca. 35% as seen in FIG. 1A.

Figure 1B:
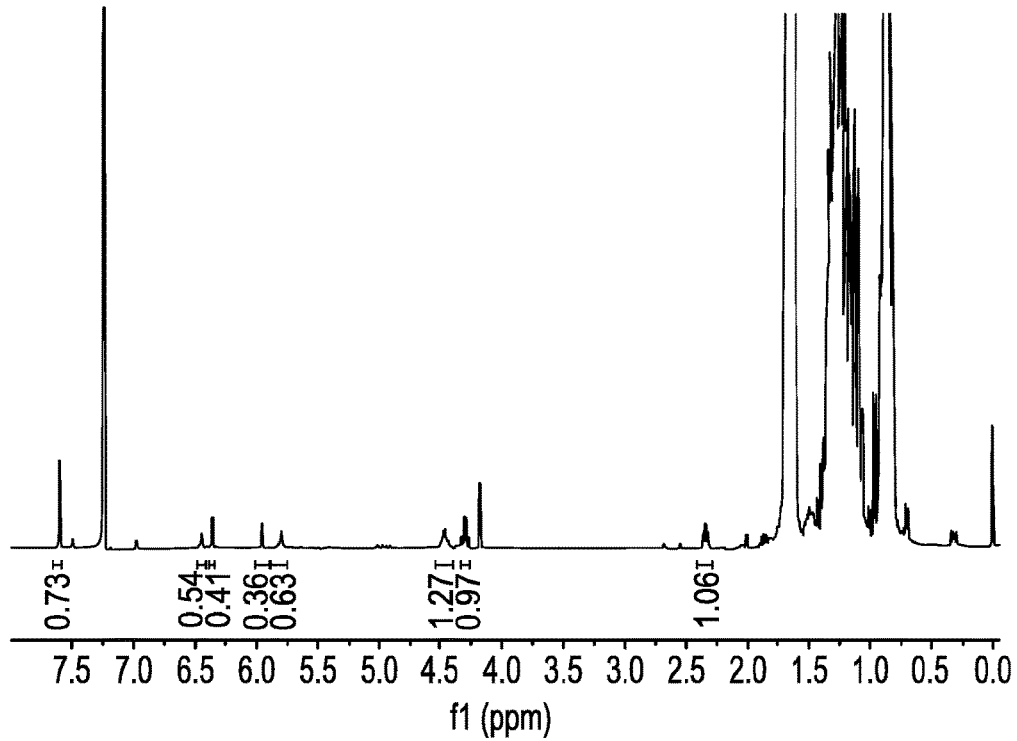

Reaction mixture was additionally heated for 6 hours at 85° C. NMR showed ca. 60% conversion with the formation of some byproduct as seen in FIG. 1B. Integration vs. internal standard gave 61% NMR yield. Further heating did not improve conversion while more byproducts were formed.

Example 2

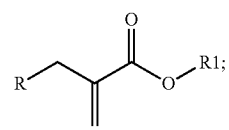

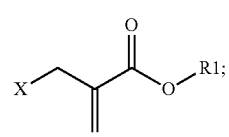

The reaction of Example 2 was performed under an inert nitrogen atmosphere glovebox and in accordance with the above reaction scheme which is non-limiting and exemplary. To the solution of methyl chloromethyl acrylate (134.6 mg) in dry methylcyclohexane (5 mL) in a 20 mL vial solution of Oct3Al (136.5 mg, 0.33 equiv) was slowly added at RT. Reaction mixture turned slightly yellow, after overnight at room temperature color disappeared. 1,3,5-tribromobenzene (71.7 mg, 0.227 mmol) was added as internal standard.

Figure 2A:
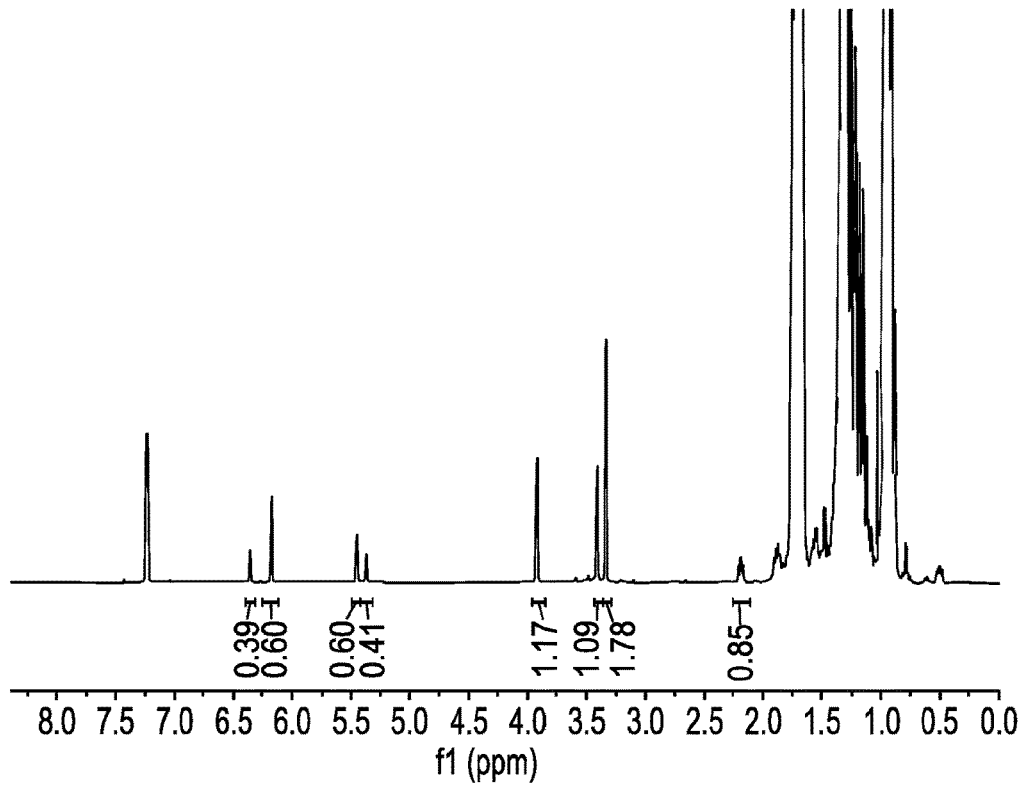
FIGS. 2A and 2B provide the NMR spectra for Example 2.

After 12 hours at room temperature the NMR conversion was calculated to be ca. 39% as seen in FIG. 2A.

Figure 2B:
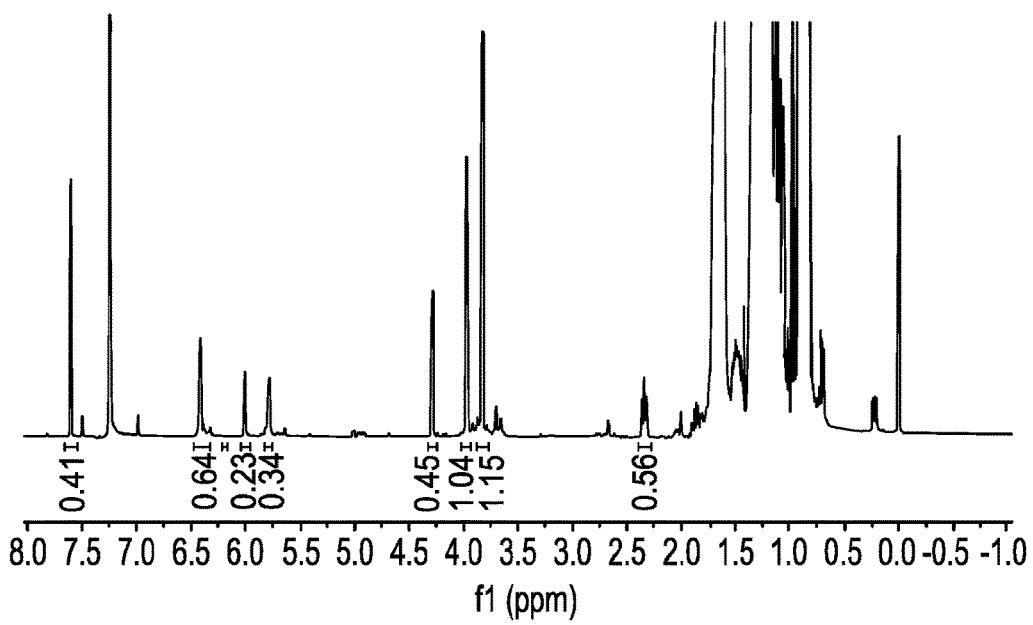

Reaction mixture was additionally heated for 6 hours at 85° C. NMR showed ca. 56% conversion with the formation of some byproduct as seen in FIG. 2B. Integration vs. internal standard gave 46-50% NMR yield. Further heating did not improve conversion, while more byproducts were formed.

What is claimed is:

1. A process for preparing an alpha-substituted acrylate, the process comprising:

a) combining starting materials comprising an alpha-(halomethyl) acrylate and an organoaluminum compound of the formula R3Al,
thereby forming a product comprising the alpha-substituted acrylate, wherein:
the alpha-substituted acrylate has the formula (I):

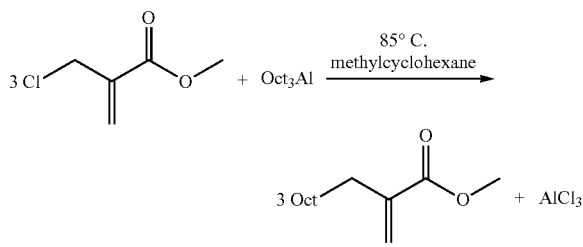

the alpha-(halomethyl) acrylate has the formula (II):

(II)

each R independently is a C1-C26 hydrocarbyl group or a polyolefinyl group;
each R1 independently is a C1-C30 hydrocarbyl group; and
X is a halogen, wherein the process excludes any transmetallation step or reaction.

2. The process of claim 1, wherein the starting materials of step a) further comprise a solvent.

3. The process of claim 2, wherein the solvent is a non-aromatic hydrocarbon solvent.

4. The process of claim 1, wherein the starting materials of step a) further comprise an organocatalyst.

5. The process of claim 1, wherein each R independently is a C1-C26 hydrocarbyl group.

6. The process of claim 1, wherein each R independently is a polyolefinyl group that can be defined by the properties of R—H, and wherein R—H has a number average molecular weight of greater than 365 g/mol.

7. The process of claim 6, wherein the polyolefinyl group is an ethylene-based polymeryl group.

8. The process of claim 7, wherein the polyolefinyl group is an ethylene homopolymeryl group comprising units derived from ethylene.

9. The process of claim 7, wherein the polyolefinyl group is an ethylene/alpha-olefin interpolymeryl group comprising units derived from ethylene and a C3-C30 alpha-olefin.

10. The process of claim 6, wherein the polyolefinyl group is a propylene-based polymeryl group.

11. The process of claim 10, wherein the polyolefinyl group is a propylene homopolymeryl group comprising units derived from propylene.

12. The process of claim 10, wherein the polyolefinyl group is a propylene/alpha-olefin interpolymeryl group comprising units derived from propylene and either ethylene or a C4-C30 alpha-olefin.

* * * * *